(12) United States Patent
Goode et al.

(10) Patent No.: US 9,131,959 B2
(45) Date of Patent: Sep. 15, 2015

(54) SPLITTABLE DILATOR DELIVERY SYSTEM

(75) Inventors: Louis B. Goode, Cranberry Township, PA (US); Chun Kee Lui, Apollo, PA (US); Robert Booker, Vandergrift, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 728 days.

(21) Appl. No.: 13/214,578

(22) Filed: Aug. 22, 2011

(65) Prior Publication Data

US 2013/0053780 A1    Feb. 28, 2013

(51) Int. Cl.
| | |
|---|---|
| A61B 17/34 | (2006.01) |
| A61F 2/97 | (2013.01) |
| A61F 2/966 | (2013.01) |
| A61F 2/95 | (2013.01) |
| A61B 19/00 | (2006.01) |

(52) U.S. Cl.
CPC ............ A61B 17/3468 (2013.01); A61F 2/966 (2013.01); A61F 2/97 (2013.01); *A61B 17/3431* (2013.01); *A61B 2019/307* (2013.01); *A61F 2/95* (2013.01)

(58) Field of Classification Search
CPC ................ A61M 25/0668; A61M 2025/0675; A61F 2/97
USPC ......... 604/164.5, 164.05, 164.1, 157–170.03, 604/264, 523–525; 606/108, 190
See application file for complete search history.

(56) References Cited

U.S. PATENT DOCUMENTS

| | | | |
|---|---|---|---|
| 4,710,181 A | 12/1987 | Fuqua | 604/280 |
| 4,776,846 A * | 10/1988 | Wells | 604/161 |
| 5,104,388 A * | 4/1992 | Quackenbush | 604/264 |
| 5,221,270 A | 6/1993 | Parker | 604/282 |
| 5,224,952 A | 7/1993 | Deniega et al. | 606/184 |
| 5,290,295 A | 3/1994 | Querals et al. | 606/108 |
| 5,318,542 A | 6/1994 | Hirsch et al. | 604/161 |
| 5,354,302 A | 10/1994 | Ko | 606/104 |
| 5,380,304 A | 1/1995 | Parker | 604/282 |
| 5,399,167 A | 3/1995 | Deniega | 604/164 |
| 5,499,975 A * | 3/1996 | Cope et al. | 604/164.1 |
| 5,534,007 A | 7/1996 | St. Germain et al. | 606/108 |
| 5,569,292 A | 10/1996 | Scwemberger et al. | 606/185 |
| 5,662,712 A | 9/1997 | Pathak et al. | 623/12 |
| 5,676,681 A | 10/1997 | Yoon | 606/185 |
| 5,873,880 A | 2/1999 | Williams et al. | 606/108 |
| 6,019,778 A | 2/2000 | Wilson et al. | 606/198 |
| 6,117,150 A | 9/2000 | Pingleton et al. | 606/167 |
| 6,368,344 B1 | 4/2002 | Fitz | 623/1.11 |
| 6,371,968 B1 | 4/2002 | Kogasaka et al. | 606/190 |

(Continued)

*Primary Examiner* — Nicholas Lucchesi
*Assistant Examiner* — Anh Bui
(74) *Attorney, Agent, or Firm* — Brinks Gilson & Lione

(57) ABSTRACT

A delivery system for an implantable member includes an elongated dilator splittable at both the proximal and distal ends. The dilator has a tapered distal end and a pair of tabs at the proximal end. An introducer for the implantable member is received in a passageway of the dilator and extends along a length of the dilator to the tapered distal end. The introducer is arranged relative to the dilator such that upon a relative proximal movement of the dilator, the tapered distal tip of the dilator splits whereby the distal end of the introducer extends therethrough. A handle has a gripping mechanism for engagement with each tab for initiating proximal movement of the dilator relative to the introducer upon rotation of the gripping mechanism. The handle is structured for splitting the dilator proximal portion upon the relative proximal movement of the dilator.

13 Claims, 9 Drawing Sheets

(56) References Cited

U.S. PATENT DOCUMENTS

| | | |
|---|---|---|
| 6,380,457 B1 | 4/2002 | Yurek et al. ............ 623/11 |
| 6,391,050 B1 | 5/2002 | Broome ............ 623/1.11 |
| 6,494,860 B2* | 12/2002 | Rocamora et al. ............ 604/43 |
| 6,514,280 B1 | 2/2003 | Gilson ............ 623/1.11 |
| 6,602,226 B1 | 8/2003 | Smith et al. ............ 604/103.05 |
| 6,663,660 B2 | 12/2003 | Dusbabek et al. ............ 623/1.11 |
| 6,689,070 B2 | 2/2004 | Hung et al. ............ 600/562 |
| 6,939,337 B2 | 9/2005 | Parker et al. ............ 604/528 |
| 7,115,138 B2 | 10/2006 | Renati et al. ............ 606/200 |
| 7,122,050 B2 | 10/2006 | Randall et al. ............ 623/1.23 |
| 7,144,386 B2 | 12/2006 | Korkor et al. ............ 604/164.03 |
| 7,232,421 B1 | 6/2007 | Gambale et al. ............ 604/57 |
| 7,258,697 B1 | 8/2007 | Cox et al. ............ 623/1.16 |
| 2001/0034514 A1 | 10/2001 | Parker ............ 604/525 |
| 2001/0037141 A1 | 11/2001 | Yee et al. ............ 623/1.11 |
| 2002/0151921 A1 | 10/2002 | Kanner et al. ............ 606/190 |
| 2002/0193863 A1 | 12/2002 | Rourke et al. ............ 623/1.11 |
| 2004/0064082 A1 | 4/2004 | LeMay et al. ............ 604/11 |
| 2004/0267203 A1 | 12/2004 | Potter et al. ............ 604/164.05 |
| 2005/0080430 A1 | 4/2005 | Wright, Jr. et al. ............ 606/108 |
| 2005/0131514 A1 | 6/2005 | Hijlkema et al. ............ 623/1.12 |
| 2005/0137448 A1* | 6/2005 | Wingler et al. ............ 600/34 |
| 2005/0165480 A1 | 7/2005 | Jordan et al. ............ 623/9 |
| 2006/0247672 A1 | 11/2006 | Vidlund et al. ............ 606/190 |
| 2007/0161956 A1 | 7/2007 | Heuser ............ 604/164.1 |
| 2007/0225659 A1* | 9/2007 | Melsheimer ............ 604/264 |
| 2009/0270969 A1* | 10/2009 | Fargahi et al. ............ 623/1.11 |
| 2012/0310167 A1* | 12/2012 | Kraus et al. ............ 604/167.03 |

* cited by examiner

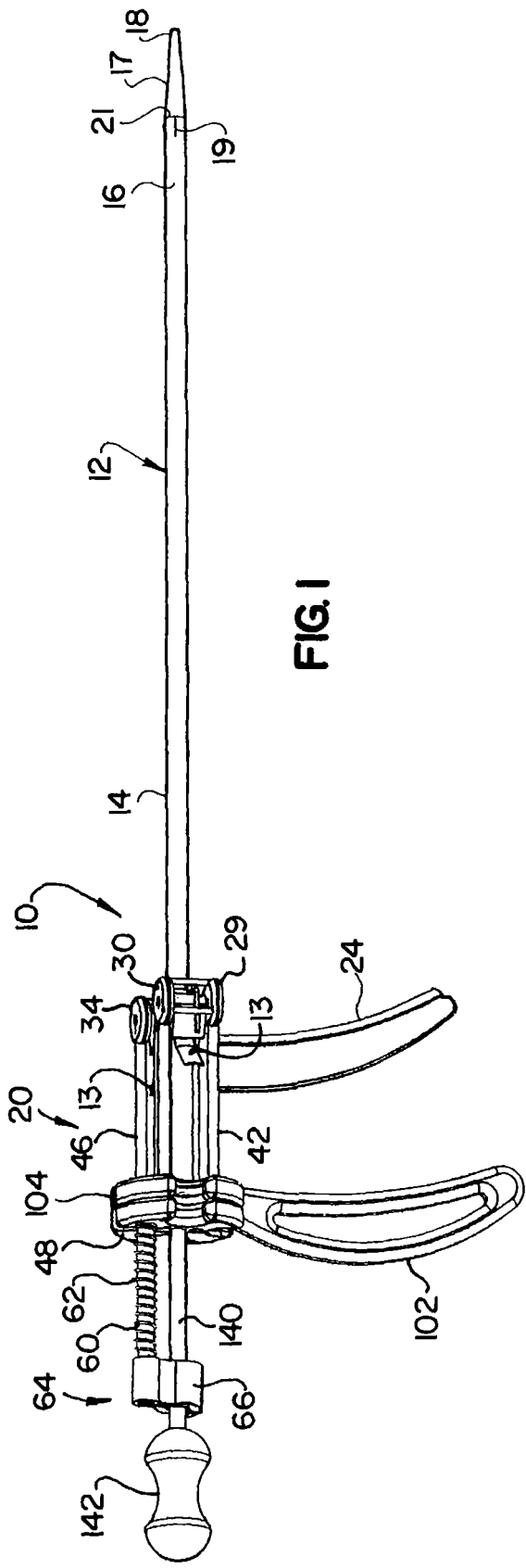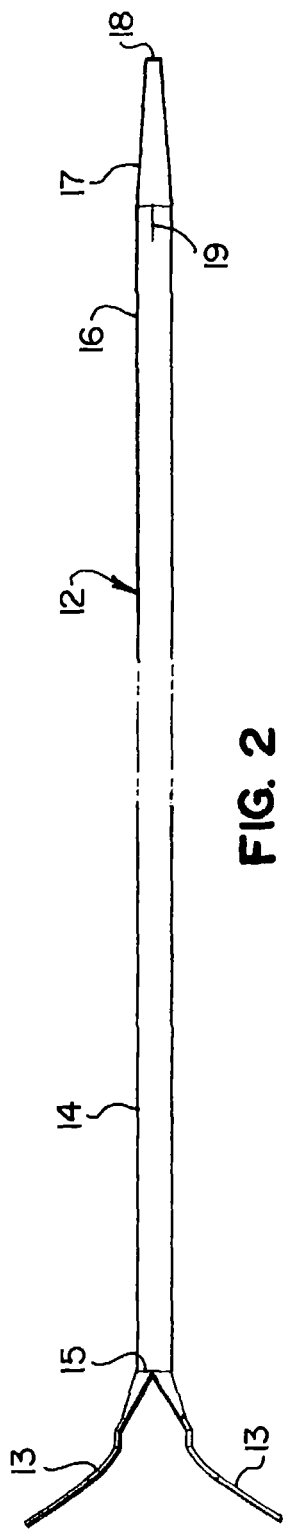

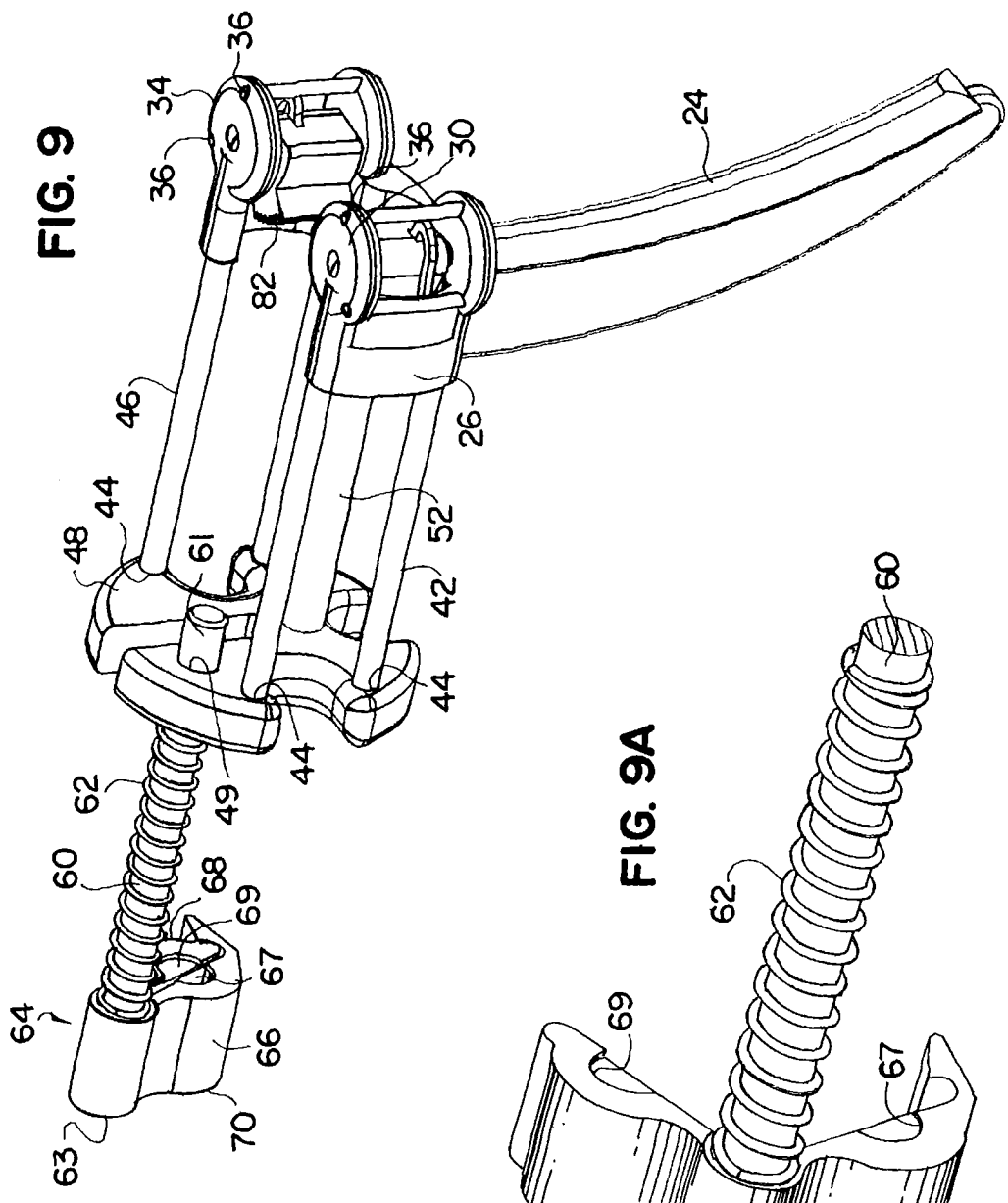

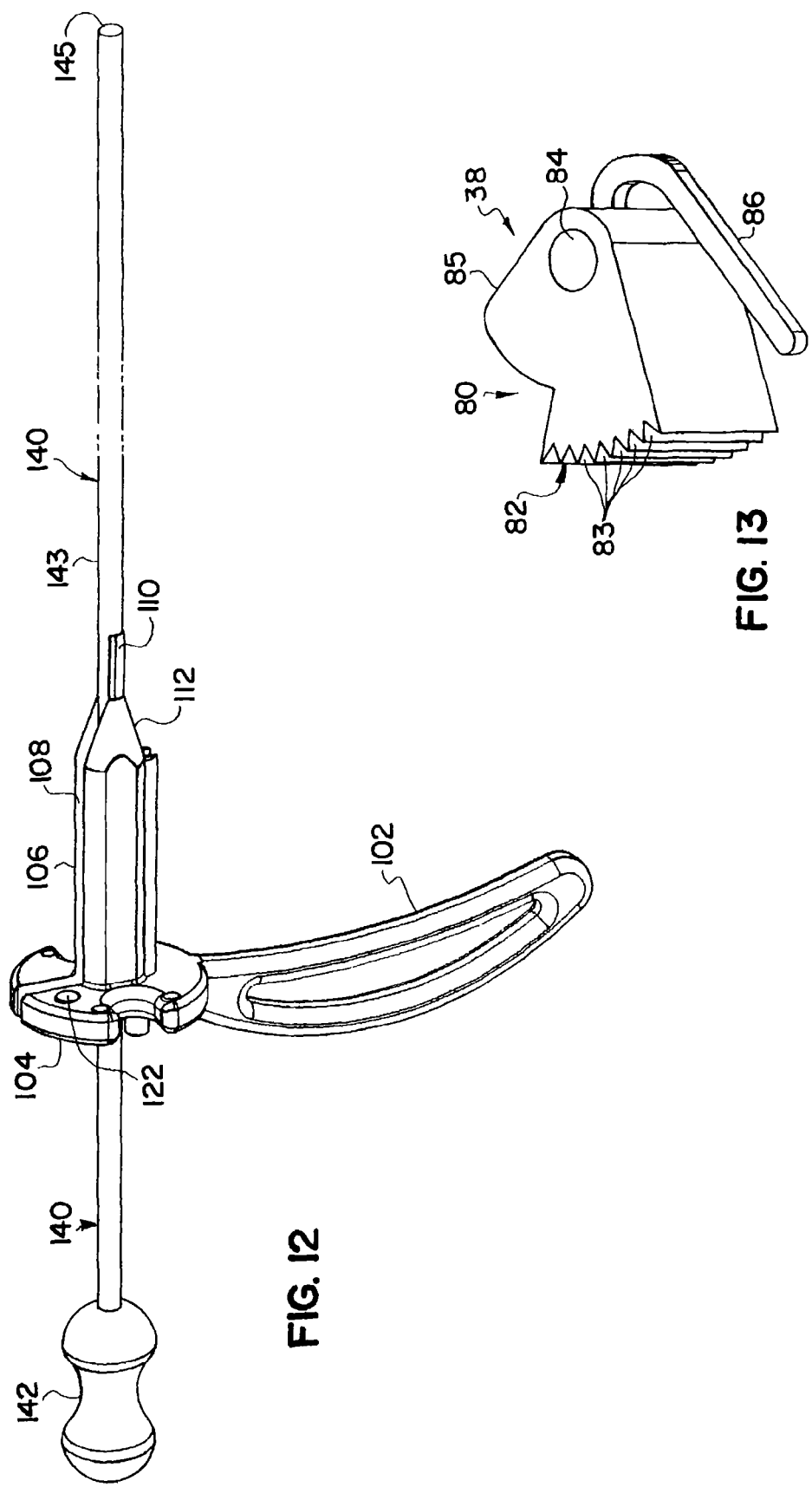

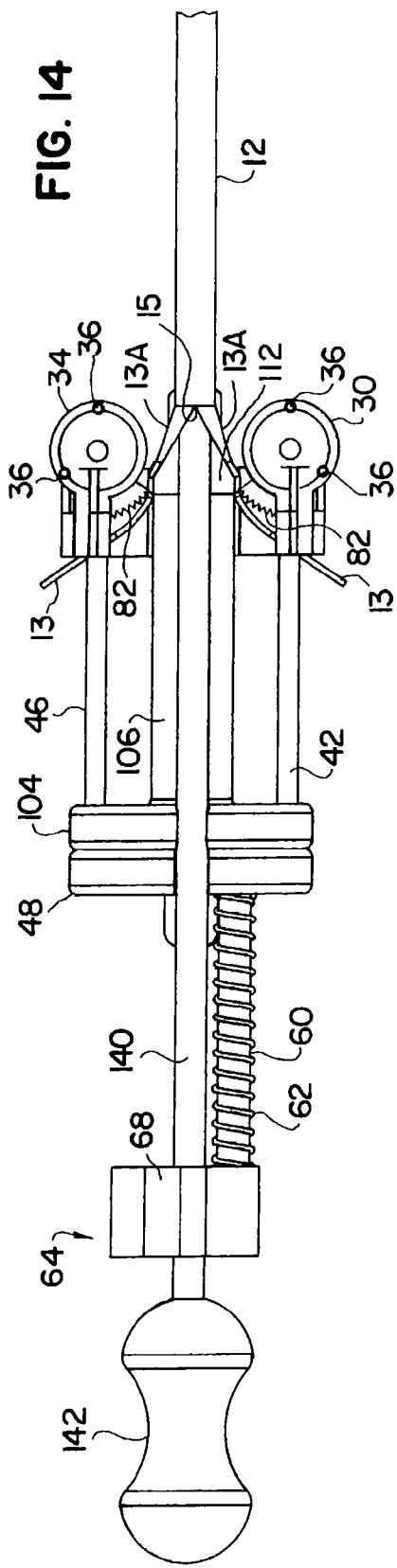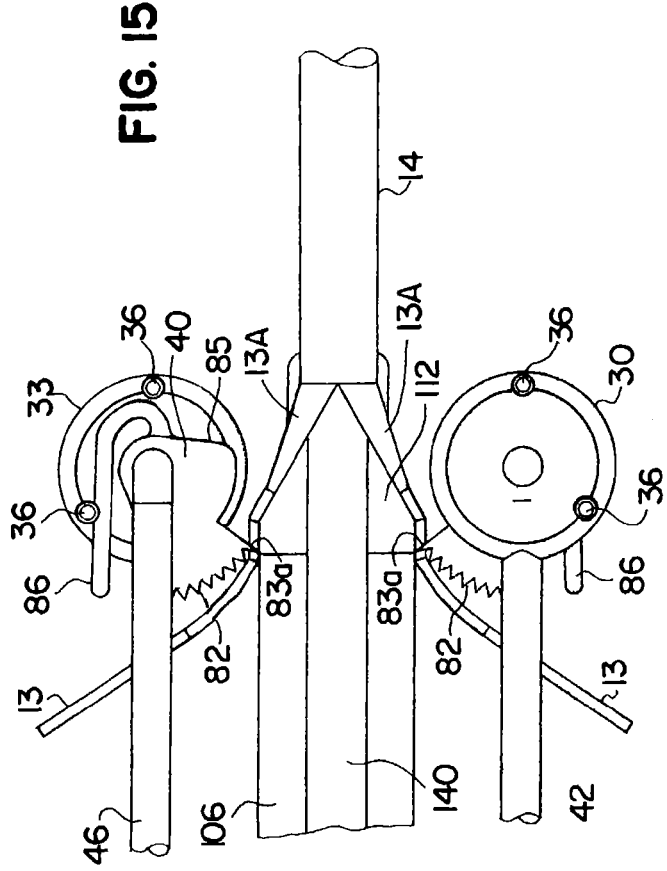

SPLITTABLE DILATOR DELIVERY SYSTEM

BACKGROUND

1. Technical Field

This invention relates to a delivery system for an implantable medical member. More particularly, the invention relates to a delivery system including a tapered dilator having a splittable portion at each of the proximal and distal ends of the dilator.

2. Background Information

Delivery devices, such as guide catheters and introducer sheaths, are widely used in the medical field as conduits for percutaneously transporting an implantable medical device through the vasculature of a patient to a target site for deployment.

Often the delivery device having the medical device positioned therein must traverse tortuous passageways in the patient's vasculature to reach the desired deployment site. A variety of introducer or delivery sheaths have been developed in an attempt to optimize this process. For example, some sheaths are formed to have different hardness levels, or durometers, along the length of the sheath. Such sheaths may have a high durometer at the proximal end, one or more intermediate sections of increasingly lower durometer, and a distal section having the lowest durometer. This arrangement enables the distal portion of the sheath to more easily bend while traversing increasingly narrow and tortuous passageways, while maintaining a higher degree of strength and rigidity at the proximal end.

Sheaths may be formed with a layered structure, which structure may include the presence of a reinforcing layer. One type of reinforcement is a helical coil that is disposed between inner and outer polymeric layers of the sheath. The presence of the coil enables the sheath to bend as it encounters a bending stress, and then return to its original orientation upon release of the stress. This type of reinforcement is also generally effective for resisting bulging of the sheath adjacent to the self-expanding stent enclosed therein. Another type of reinforcement is a woven braid. A braided reinforcement enhances the torqueability of the sheath as it traverses the passageway. Sheaths may be formed to combine one or more features of the aforementioned designs, as well as other features that may be added for a particular purpose.

Regardless of the particular construction of the introducer device, the introducer is typically housed within a passageway of a tapered dilator for introduction into a body passageway. The tapered dilator facilitates passage through tortuous passageways within the body. Once this delivery system comprising the dilator and the introducer sheath reaches the target site, it is desirable to remove the dilator from the introducer sheath prior to deployment of the medical device. Removal of the dilator from the introducer can be problematic, and many prior art attempts have been made to facilitate such removal. One such attempt comprises providing a dilator having a frangible distal tip. With this design, the dilator can be peeled away from the introducer sheath upon splitting of the tapered distal tip of the dilator. Although this apparatus works well in some instances, it performs less so in other instances. One such instance involves removal of the dilator from an implantable device having a large proximal end (e.g., a pacemaker lead). The presence of the large proximal end impedes peeling away of a sheath that has been split only at the distal end.

It is desired to provide a delivery system for use in delivering an implantable medical device to a target site within the body of a patient, and wherein the dilator is more easily removed from around the introducer when compared to existing systems.

BRIEF SUMMARY

The present invention addresses the shortcomings of the prior art. In one form thereof, the invention comprises a delivery system for deploying an implantable medical member to a target site within the body of a patient. The delivery system includes an elongated dilator having a proximal portion, a distal portion, and a passageway extending therebetween. The proximal portion includes at least one tab extending from a proximal end thereof. The distal portion tapers to a distal tip, wherein the distal portion is splittable to facilitate delivery of the implantable medical member to the target site. An introducer has a proximal portion and a distal portion. The proximal portion extends to a proximal end and the distal portion extends to a distal end. The introducer distal portion is received in the dilator passageway and extends substantially along a length of the dilator to the tapered distal portion. The introducer is structured and arranged relative to the dilator such that upon a proximal movement of the dilator relative to the introducer, the tapered distal tip of the dilator splits whereby the introducer distal portion extends through the split dilator portion. The introducer proximal end extends beyond the dilator proximal portion in a proximal direction, and the introducer is dimensioned for receiving the implantable member therein. A handle mechanism is arranged to receive the proximal portion of the dilator. The handle mechanism includes a respective gripping mechanism engaged with each of the at least one tab for initiating the proximal movement of the dilator relative to the introducer upon a rotation of the gripping mechanism, and an activator engaged with the gripping mechanism for initiating the rotation of the gripping mechanism upon activation thereof.

In another form, the invention comprises a delivery system for delivering an implantable member to a target site in the body of a patient. The delivery system comprises a splittable elongated dilator having a proximal portion, a distal portion, and a passageway extending therebetween dimensioned for receiving the implantable member therein. The proximal portion includes a pair of tabs extending therefrom. The distal portion extends to a tapered distal tip, and is structured for splitting to facilitate delivery of the implantable member to the target site. A handle is engaged with the dilator proximal portion. The handle includes a respective gripping mechanism engaged with each of the tabs for initiating a proximal movement of the dilator upon activation of the gripping mechanisms, and an activator for the gripping mechanisms. The handle includes a structure for splitting the proximal portion of the dilator upon the proximal movement of the dilator.

In yet another form, the invention comprises a method for delivering an implantable member to a target site within the body of a patient. A delivery system is arranged along an entry opening in the body. The delivery system comprises an elongated dilator having a proximal portion, a distal portion, and a passageway extending therebetween. The proximal portion includes a pair of tabs extending from a proximal end thereof. The distal portion tapers to a distal tip configured for insertion into the entry opening, and is splittable to facilitate delivery of the implantable member to the target site. An introducer has a proximal portion and a distal portion. The proximal portion extends to a proximal end and the distal portion extends to a distal end. The introducer distal portion is received in the dilator passageway and extends substantially along a length of the dilator to the tapered distal portion. The introducer proximal end extends beyond the dilator proximal portion in a proximal direction. The introducer is dimensioned for receiving the implantable member therein. A handle mechanism is arranged to receive the proximal portion of the dilator. The handle mechanism includes a respective gripping mechanism engaged with each of the tabs for initiating a proximal movement of the dilator relative to the introducer upon a rotation of the gripping mechanisms, and a trigger member engaged with the gripping mechanisms. The distal portion of the dilator is inserted into the entry opening, and directed to the target site. The trigger member is activated to rotate the gripping mechanisms engaged with the tabs for initiating the proximal movement of the dilator relative to the introducer, wherein the tapered distal tip of the dilator splits such that the introducer distal portion extends through the split dilator portion. The implantable member may then be delivered to the target site through the introducer distal portion. If desired, the handle mechanism may further comprise an elongated nose portion wherein the nose portion includes a distally tapered portion structured and arranged to receive the dilator proximal portion upon the proximal movement of the dilator, and configured such that the dilator proximal portion splits upon movement thereover. The implantable member may be an implantable medical device, or a capsule or pellet containing a medicament.

BRIEF DESCRIPTION OF THE DRAWINGS

FIG. 1 is a perspective view of a delivery system according to an embodiment of the present invention;

FIG. 2 is a side view of the dilator of the delivery system of FIG. 1;

FIG. 9 is a perspective view of the trigger portion as shown in FIG. 5;

FIG. 9A is a view of the clamp utilized in the trigger portion, wherein the clamp is in the open position;

FIG. 12 is a side view of the nose portion of the delivery system, also showing the presence of the introducer;

FIG. 13 is a perspective view of a gripper body;

FIG. 14 is a top view of a portion of the delivery system illustrating the position of the tabs relative to the jaws of the respective gripper bodies;

FIG. 15 is an enlarged view of a portion of the delivery system as shown in FIG. 14, with portions removed to facilitate visualization of the position of the jaws relative to the tabs;

DETAILED DESCRIPTION OF THE DRAWINGS AND THE PRESENTLY PREFERRED EMBODIMENTS

Figure 3:
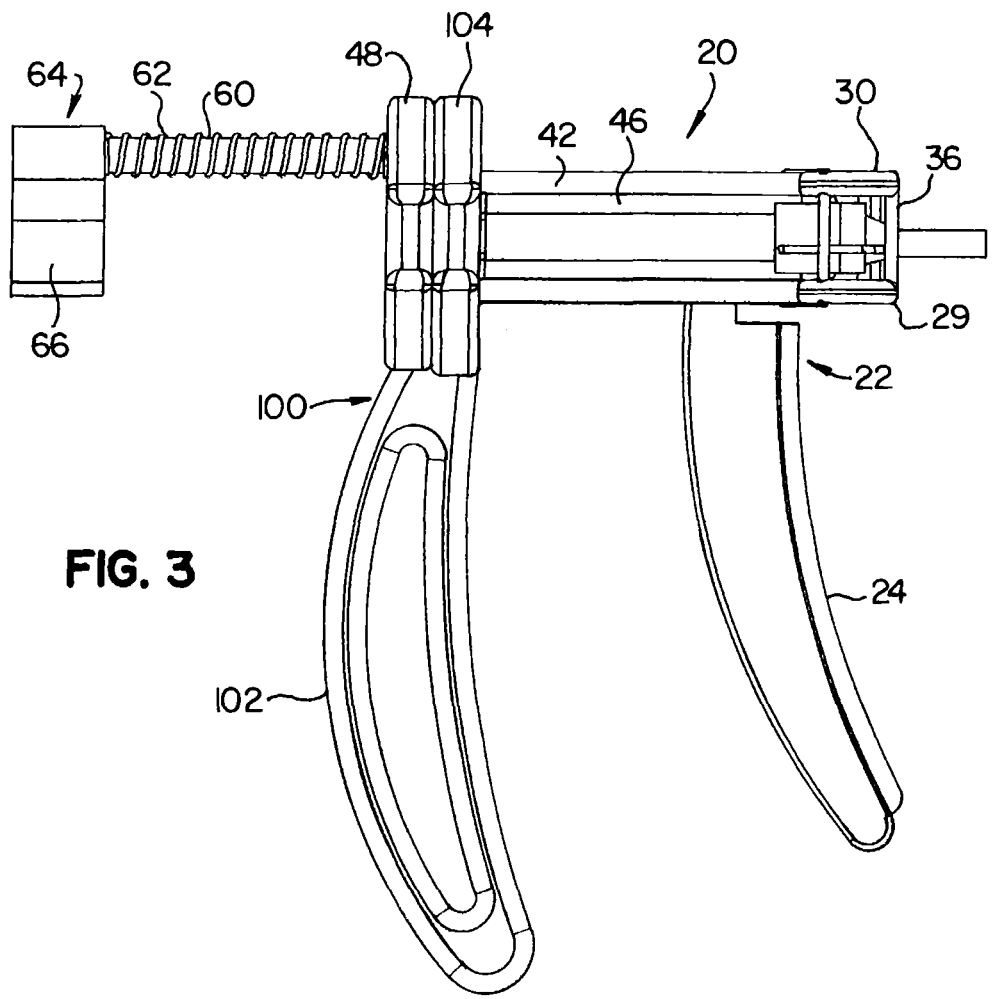
FIG. 3 is a side view of the handle mechanism of the apparatus of FIG. 1.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of a delivery system, as well as the axial ends of other component features of the delivery system. The term "proximal" is used in its conventional sense to refer to the end of the delivery system, or component, that is closest to the operator during use of the delivery system. The term "distal" is used in its conventional sense to refer to the end of the delivery system, or component, that is initially inserted into the patient, or that is closest to the patient during use.

FIG. 1 illustrates a perspective view of a delivery system 10 according to an embodiment of the present invention. Delivery system 10 may be used for delivering an implantable member to a target area in the body of a patient. As shown, delivery system 10 includes a dilator 12, and a handle mechanism 20. An introducer 140 is received in a passageway extending through dilator 12 in well-known fashion.

In the embodiment shown in FIG. 1, the implantable member (not shown) is received in a passageway extending through introducer 140. Those skilled in the art are well aware of implantable members that are commonly delivered to a target site in the body, which members may also be delivered by the inventive delivery system. The implantable member may comprise a medical device, such as a stent, a cardiac lead (e.g., a pacemaker lead or a defibrillator lead), etc., intended for delivery to a target site, e.g., in the vasculature or other cavity or opening in the body of the patient. Alternatively, the implantable member may comprise a capsule or pellet containing a medicament. Capsules or pellets containing a medicament may be delivered directly to a target site, for example, to the abdominal cavity through a puncture in the abdominal wall, or to a cavity in the brain. Alternatively, such medicaments may be delivered directly into tissue of a target site. Those skilled in the art will appreciate that other implantable members may also be delivered to various target sites within the body utilizing the splittable delivery device as described and shown herein.

Dilator 12 is illustrated in FIG. 2. Dilator 12 includes a proximal portion 14 and a distal portion 16. Proximal portion 14 extends to a proximal end 15. In the non-limiting embodiment shown, a pair of flexible tabs 13 extend in the proximal direction from proximal end 15 of the dilator. Distal portion 16 includes a tapered portion 17 that tapers to distal tip 18. Typically, distal tip 18 will be dimensioned to allow passage of a wire guide (not shown) therethrough. Dilator 12 may be formed of any composition commonly used in the art for such purposes in delivering a medical device to a target site. Non-limiting examples of suitable compositions for the dilator include polytetrafluoroethylene (PTFE), polypropylenes, and polyamides (nylons).

Tapered portion 17 may be formed as an integral part of the dilator 12, or alternatively, may be separately formed and thereafter attached to the distal end of the dilator. The distal tip portion is molded or otherwise formed to the desired size and shape, and thereafter bonded or otherwise securely attached (such as by gluing) to the distal-most end of the dilator. As illustrated, tapered portion 17 tapers from a larger diameter to a smaller diameter in the distal direction. The use of a tapered tip facilitates distal movement of the dilator through the desired pathway (such as the vasculature) through the body of the patient. Such a tip has the structural integrity necessary to negotiate tortuosity through the vessel, and to deflect the dilator as it traverses the pathway.

As illustrated in FIGS. 1 and 2, one or more longitudinally weakened areas 19 are provided along dilator distal portion 16. Preferably, weakened areas 19 are provided as longitudinal slits along distal portion 16, immediately adjacent tapered portion 17. More preferably, a weakened area 19 is provided as a longitudinal slit along each longitudinal side of distal portion 16 immediately adjacent tapered portion 17 (only one of which is visible in the orientation of FIG. 1).

As another alternative, one or more weakened areas can be provided along the proximal length of tapered portion 17 instead of, or in addition to, the weakened areas provided along the longitudinal side of distal portion 16, as shown and described. As a still further alternative, the weakened areas can comprise respective radial slits, or score lines, that extend partially through distal tip portion 17. These slits may extend the entire length, or any segment thereof, of the outer surface of tapered tip portion 17, but stop short of extending radially through the inner surface. Those skilled in the art are well aware of suitable methods for providing weakened areas along tubular medical devices to facilitate a controlled splitting of the device. Some examples of weakened areas are described in U.S. Patent Publ. No. 2007/0225659, incorporated by reference herein.

Longitudinally weakened areas 19 enable the distal tip portion to be split upon exposure to a stressor. Thus, upon passage of, e.g., a medical device or an introducer 140, through weakened areas 19 of sheath distal portion 16, the tip splits (FIG. 16) along the weakened areas into a plurality of discrete axial segments. The number of discrete split segments depends upon the number of weakened areas 19 distributed along the circumference of the sheath distal portion 16 and/or tapered portion 17. Those skilled in the art will appreciate that the weakened portions described herein are only examples of modifications that can be made to the distal portion of a sheath to facilitate splitting, and that other arrangements that accomplish the desired function are also contemplated.

Figure 4:
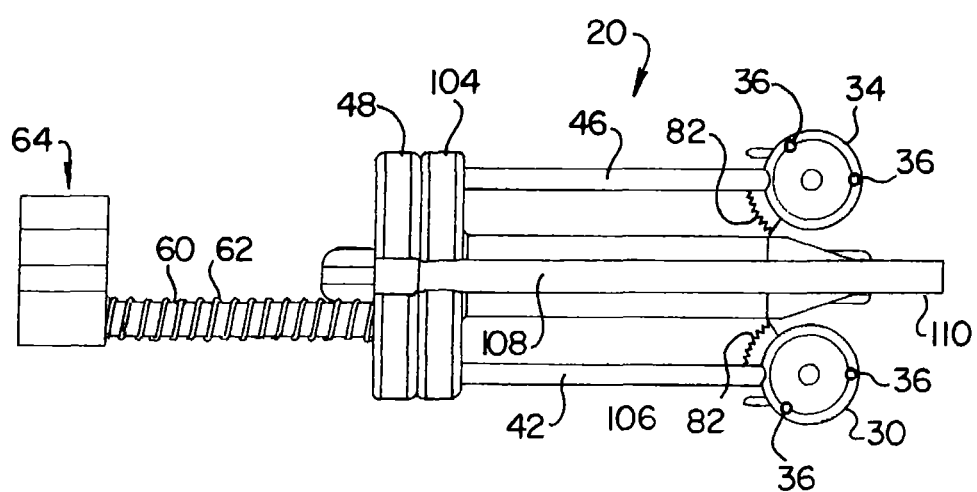
FIG. 4 is a top view of the handle mechanism.
Figure 5:
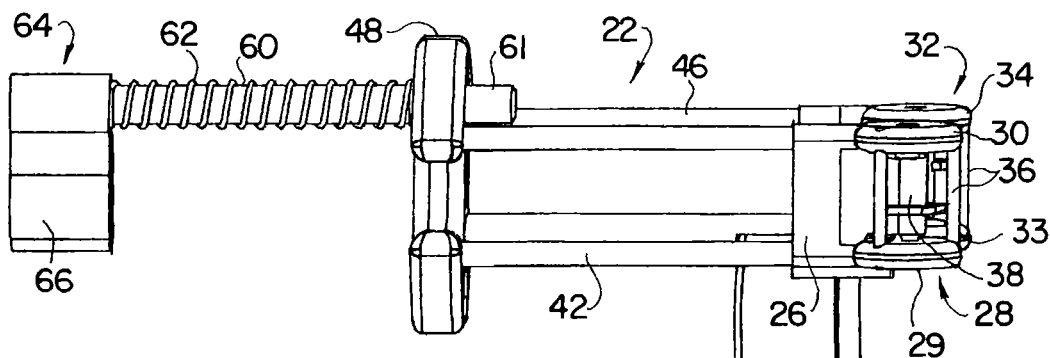
FIG. 5 is a side view of the trigger portion of the handle mechanism of FIG. 3.
Figure 6:
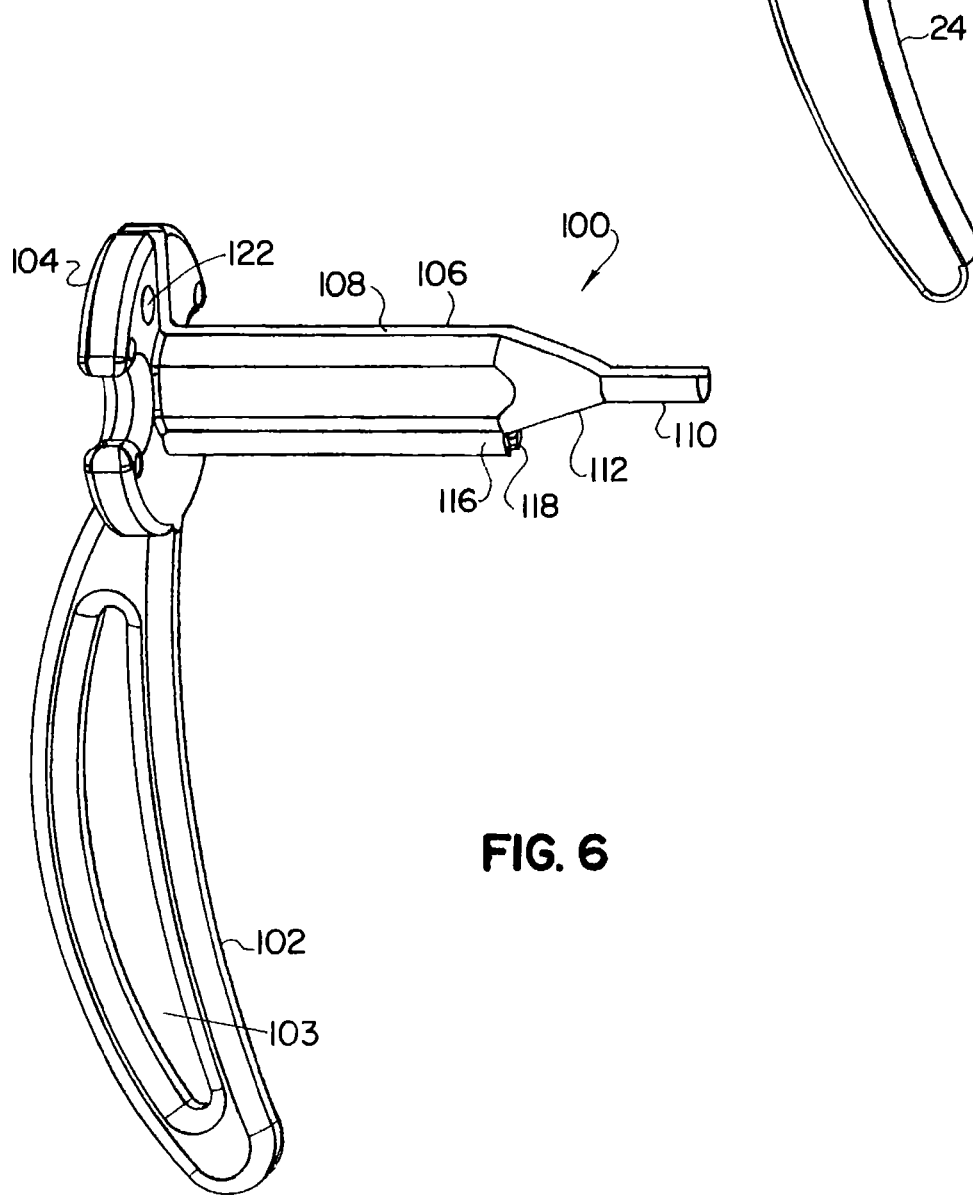
FIG. 6 is a side view of the nose portion of the handle mechanism of FIG. 3.

FIGS. 3-12 illustrate features of the handle mechanism 20. FIG. 3 illustrates a side view of the handle mechanism. FIG. 4 illustrates a top view of the handle mechanism. Handle mechanism 20 includes a trigger portion 22 and a nose portion 100. FIG. 5 illustrates a side view of trigger portion 22, and FIG. 6 illustrates a side view of nose portion 100.

Figure 7:
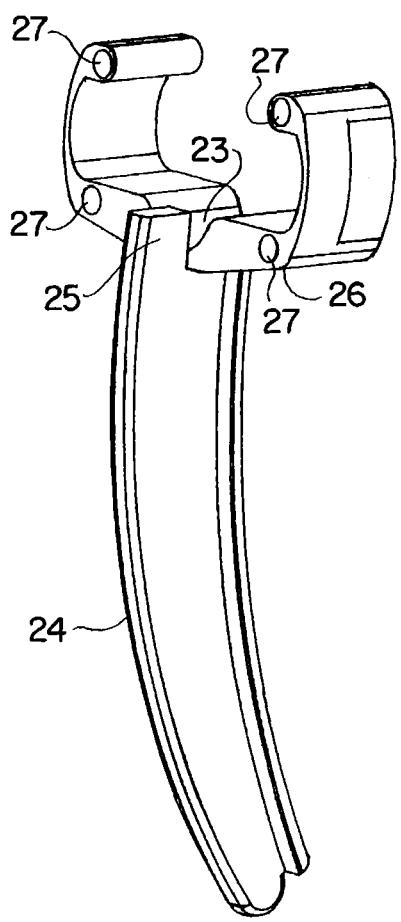
FIG. 7 illustrates the trigger grip and the nose support of the trigger portion shown in FIG. 5.

Trigger portion 22 includes a trigger grip 24. Trigger grip 24 is configured to enable an operator's hand to easily wrap around the trigger grip for activation of the handle mechanism, as described herein. As best shown in FIG. 7, trigger grip 24 includes a slotted upper portion 25 that fixedly receives nose support portion 26.

Nose support portion 26 receives a pair of frames 28, 32 (FIG. 5) that support respective rotatable gripper bodies 38, 40. Frame 28 comprises support disks 29, 30, and frame 32 comprises support disks 33, 34. A plurality of pins 36 (FIGS. 3, 4) or other suitable structure are provided for attaching support disks 29 and 30, and support disks 33 and 34, respectively.

Figure 8:
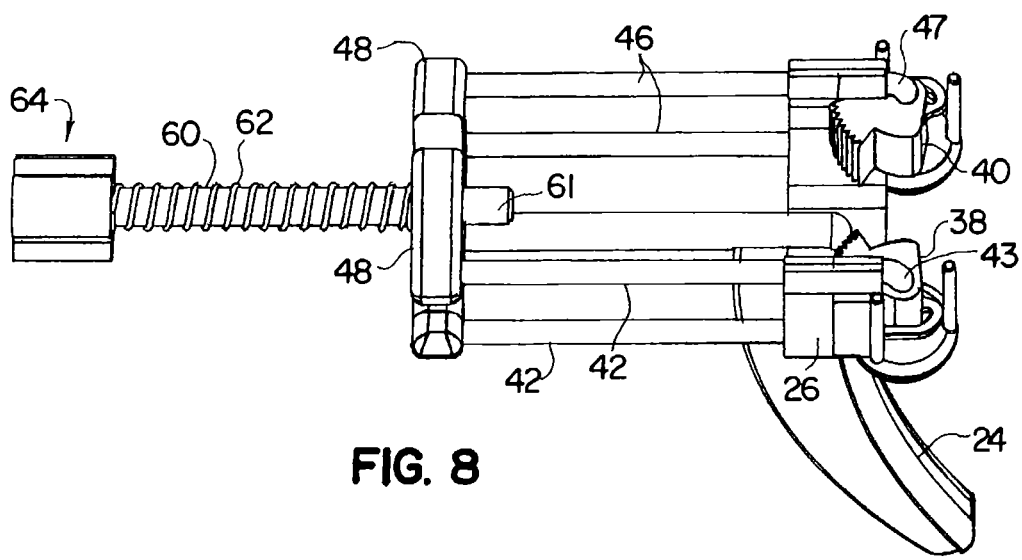
FIG. 8 illustrates the gripper bodies housed in the frames of the trigger portion shown in FIG. 5.

Gripper body 38 is housed in frame 28, and gripper body 40 is housed in frame 32. The position and configuration of the gripper bodies in the respective frame is best shown in FIG. 8. In the view shown in FIG. 8, upper support disks 30 and 34 have been removed for clarity. A perspective view of a gripper body, in this case gripper body 38, is shown in FIG. 13. As shown, gripper body 38 comprises a generally elastomeric main body portion 80. In the non-limiting embodiment shown, body portion 80 includes jaw portion 82 comprising a plurality of teeth 83, a passageway 84 extending through the gripper body, a stop portion 85, and a tail 86. Gripper body 40 is identical to gripper body 38. Examples of materials suitable for the gripper bodies include plastic acetals or ABS, as well as metals or metal alloys, such as stainless steel or titanium. The gripper bodies can be plastic or metal injection molded, or can be machined in conventional fashion to the desired configuration.

As further shown in FIG. 8, a pair of capture rods 42, 46 extend between gripper bodies 38, 40 and slotted drive ring 48 for maintaining the gripper bodies 38, 40 in position in frames 28, 32. Each capture rod 42, 46 comprises a generally U-shaped structure, wherein the free ends of the U-shape are fixedly received in respective apertures 44 in drive ring 48 (FIG. 9). The curved ends 43, 47 of respective U-shaped capture rods 42, 46 extend through respective apertures 27 in nose support portion 26 (FIGS. 7, 8), and respective passageways 84 in gripper bodies 38, 40 (FIG. 13). Preferably, the capture rods are made of a metal or alloy such as stainless steel, and the support disks are made of a rigid plastic. Those skilled in the art will appreciate that other compositions capable of acting in the nature of a metal or alloy, or a rigid plastic may be substituted.

Figure 10:
FIG. 10 is a segment of the trigger portion showing features of the slotted drive ring.

Slotted drive ring 48 is best shown in FIGS. 9 and 10. As best shown in FIG. 10, a slotted trigger rod 52 interconnects drive ring 48 and trigger grip 24. Trigger rod slotted portion 53 receives upper trigger portion 25, and is received along cradle portion 23 of nose support portion 26 (FIG. 7). As shown in FIG. 9, holder rod 60 interconnects slotted drive ring 48 and clamp 64. Holder rod 60 is slidably received in aperture 49 (FIG. 10) in slotted drive ring 48. As described herein, end 61 of holder rod is fixedly received in aperture 122 of slotted nose ring 104 (FIG. 6). Drive spring 62 rides along holder rod 60 between drive ring 48 and clamp 64.

Clamp 64 comprises respective first latch 66 and second latch 68. Latch halves 66, 68 join in conventional fashion to define an aperture 63 for receiving an end of holder rod 60, and an aperture 70 for receiving introducer 140, as described herein. FIG. 9A illustrates clamp 64 in the open position. In this embodiment, second latch 68 is pivotable along hinge 65 to enable the clamp to be selectively maneuvered between the respective open and closed positions. First and second gripping pads 67, 69 are provided in aperture 70. The gripping pads can be formed from silicone or other elastomer that is capable of gripping and holding the captured device in a manner that does not crush, dent, or otherwise damage the device. The respective latches 66, 68 are made of plastic and can be injection molded or machined. Non-limiting examples of suitable plastic include acetal resins such as DELRIN®, ABS and polycarbonates.

Figure 11:
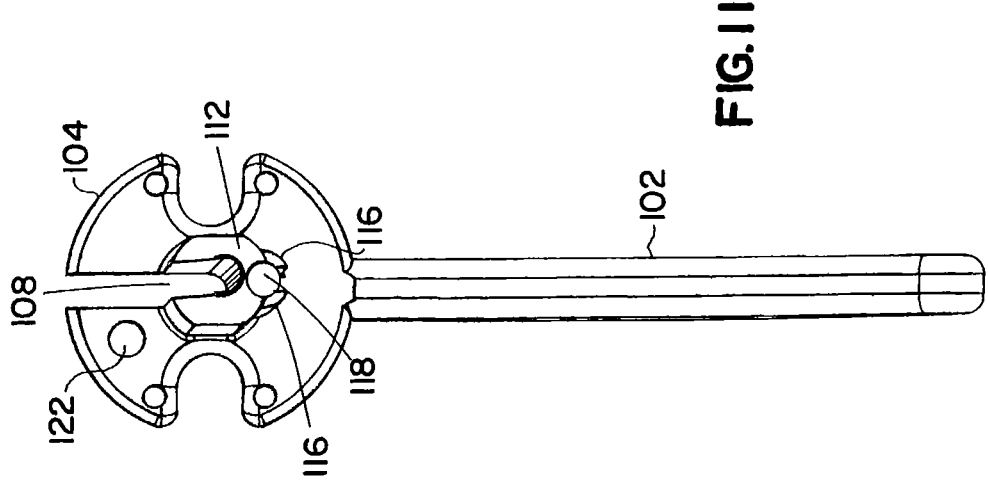
FIG. 11 is an end view of the nose portion, as viewed distally of the nose portion.

As stated above, FIG. 6 illustrates a side view of nose portion 100. FIG. 11 illustrates an end view of nose portion 100, as viewed from the distal end thereof. Nose portion 100 includes nose grip 102, and slotted nose ring 104 fixedly connected to nose grip 102. Nose grip 102 may be configured in any manner to allow convenient gripping by the operator, and may include a void 103 along an interior space thereof. Except as described herein, the configuration of slotted nose ring 104 generally corresponds to that of slotted drive ring 48 as shown, e.g., in FIGS. 1, 3, and 4. Slotted drive ring 48 and slotted nose ring 104 are also typically formed of plastic, such as the plastics described above (DELRIN®, ABS and polycarbonates).

Nose portion 100 includes an elongated nose extension 106 extending in a distal direction from slotted nose ring 104. Nose extension 106 preferably includes a tapered portion 112 extending to a smaller diameter distal end portion 110. A slot 108 extends therealong for slidably receiving introducer 140, as described below. Nose extension 106 also includes a pair of winged extenders 116 that define slot 118. Slot 118 is dimensioned to slidably receive trigger rod 52. Aperture 122 fixedly receives holder rod 60, as described above.

Introducer 140 is slidably received along nose extension slot 108, as best shown in FIG. 12. In FIG. 12, the features of the dilator 12, trigger portion 22 and the clamp 64 have been omitted to better illustrate the position of the introducer 140 relative to the nose portion. Introducer 140 includes a grasping portion 142 at a proximal end thereof to enable manipulation by the operator, as described herein. The main body portion 143 of the introducer distal of nose extension 106 is slidably received within the passageway extending through dilator 12. Preferably, introducer 140 has a length such that distal tip 145 extends interiorly of dilator 12 to a junction 21 between elongated distal portion 16 and tapered portion 17. Introducers are well known in the medical arts, and introducer 140 can be of any such composition. Non-limiting examples of suitable compositions include a polytetrafluoroethylene (PTFE) body with a stainless steel or titanium distal portion. Another example includes a PTFE inner liner wrapper by a conventional reinforcing member, such as a braid or a coil, and having an outer jacket formed from a polyether block amide or a polyamide (nylon). One example of a suitable introducer is described in U.S. Pat. No. 5,380,304 incorporated by reference herein.

Additional features of delivery system 10 will become clear as a result of the following discussion of the operation of the system. FIG. 1 illustrates the delivery system in the initial, neutral position prior to activation of the handle for splitting dilator 12. FIG. 14 is a top view of delivery system 10 in the neutral position of FIG. 1. FIG. 15 is an enlarged view of a portion of the delivery system as shown in FIG. 14. Upper support disk 34 and nose support portion 26 have been removed from the view of FIG. 15 to better illustrate the position of the jaws relative to the tabs in the neutral position. The distal end of introducer 140 is received within the passageway extending through dilator 12. The proximal end of introducer 140 is clamped in place by closing respective latches 66 and 68 around the introducer.

FIGS. 14 and 15 illustrate the position of tabs 13 when dilator 12 is loaded onto handle 20 in the neutral position. As shown, each one of tabs 13 is threaded along handle mechanism 20, such that a respective tab 13 is held in place between a respective gripper body jaw 82 and nose extension 106. A more distal portion 13A of each of the tabs 13 is received over nose extension tapered portion 112. As shown, the leading tooth 83a of each jaw 82 engages tab 13 under slight tension. This tension may be created by the position of tail 86 relative to pin 36, as best shown in FIG. 15.

The operator activates trigger portion 22 by pulling trigger grip 24 in the proximal direction. In order to carry out this operation, the operator grasps respective nose grip 102 and trigger grip 24 with one hand, and exerts a grasping force against the trigger grip in well-known fashion. This action causes trigger grip 24, and therefore the features of trigger portion 22 (FIG. 5), to slide in the proximal direction relative to the nose grip.

Figure 16:
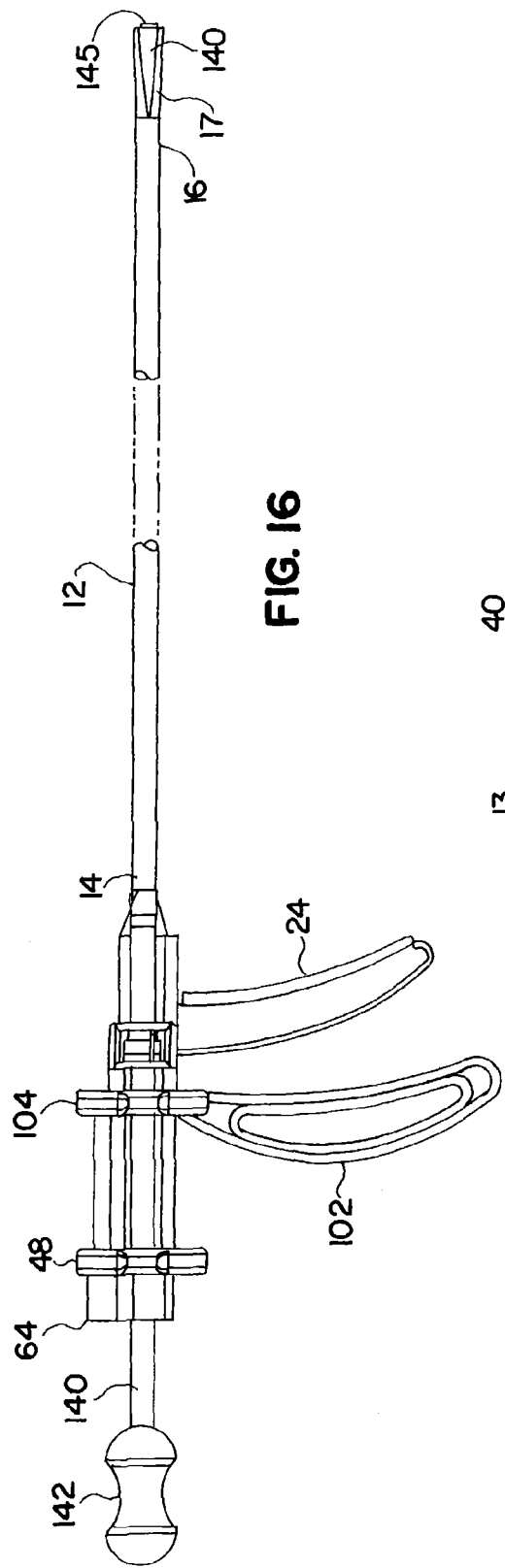
FIG. 16 is a side view of delivery system following an initial trigger pull.
Figure 17:
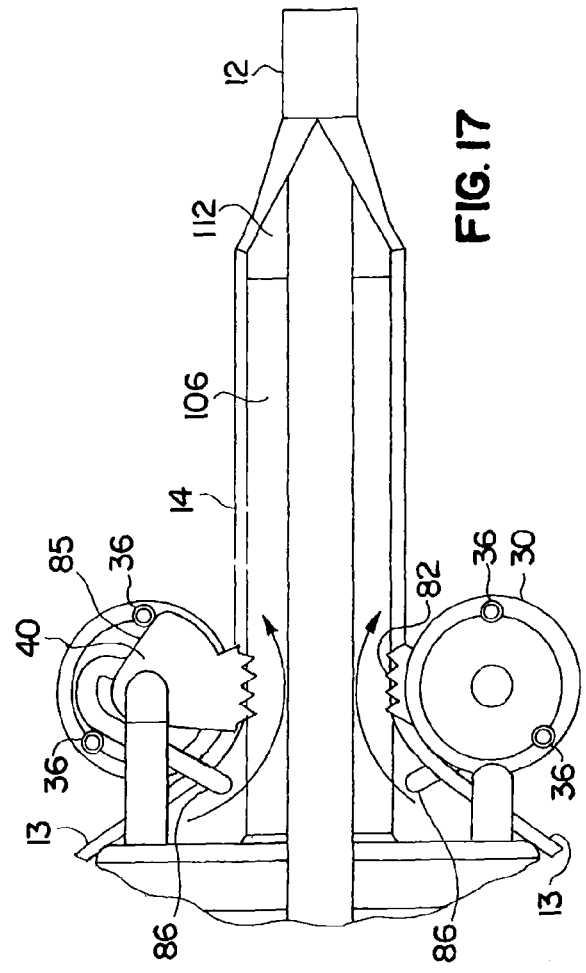
FIG. 17 is an enlarged top view of a portion of the delivery system as shown in FIG. 16 following an initial trigger pull.

FIG. 16 illustrates a side view of delivery system 10 following an initial trigger pull. FIG. 17 illustrates an enlarged top view of a portion of the delivery system as shown in FIG. 16, and illustrates the full engagement of the teeth of each jaw 82 of the respective gripper body 38, 40 with respective tab 13. This engagement is maintained throughout the trigger pull. As in FIG. 15, support disk 34 and nose support portion 26 have been removed from the view of FIG. 17 to better illustrate the position of the jaws relative to the tabs following the initial trigger pull. Movement of trigger 24 in the proximal direction as described above causes respective jaws 82 of the respective gripper body to dig into respective tabs 13, and rotate (in the direction of the arrows in FIG. 17) until stop portion 85 meets the pin 36 as shown. Such rotation causes dilator 12 to be pulled in the proximal direction. Additionally, as trigger portion 22 (including drive ring 48) slides in the proximal direction as described, spring 62 is compressed between clamp 64 and drive ring 48 (FIG. 16). If desired, clamp 64 and drive ring 48 can be provided with recesses to receive respective axial ends of compressed spring 62.

As dilator 12 is pulled in the proximal direction, proximal dilator portion 14 advances over tapered portion 112 of nose extension 106. This action causes dilator 12 to split along its proximal length, as shown in FIG. 17. In addition, upon the initial trigger pull the distal portion 17 of the dilator begins to split at the taper 17. This split occurs as the dilator is pulled in the proximal direction over the distal tip 145 of the introducer 140, as shown in FIG. 16, or alternatively, over the distal end of an implantable medical device. As a result, the distal end of the dilator is completely split at the taper.

Upon release of the trigger, the spring 62 biases trigger portion 22 (including drive ring 48) in the distal direction to return to the at-rest neutral position shown in FIGS. 14, 15. Gripper bodies 38, 40 rotate in the opposite direction from that shown in the arrows in FIG. 17 such that they also return to the neutral position. Successive trigger pulls will continue to split the dilator at both the proximal end 14 and distal end 16 until the dilator 12 is completely split. At this time, the split portions of the dilator may be readily slid or peeled off the introducer.

After the dilator has been completely split and removed, clamp 64 can be released from introducer 140, and handle mechanism 20 can be removed.

It is intended that the foregoing detailed description be regarded as illustrative rather than limiting, and that it be understood that it is the following claims, including all equivalents, that are intended to define the spirit and scope of this invention.

The invention claimed is:

1. A delivery system for deploying an implantable medical member to a target site within the body of a patient, comprising: an elongated dilator having a proximal portion, a distal portion, and a passageway extending therebetween, said proximal portion including at least one tab extending from a proximal end thereof, said distal portion tapering to a distal tip, said distal portion being splittable to facilitate delivery of said implantable medical member to said target site; an introducer having a proximal portion and a distal portion, said proximal portion extending to a proximal end and said distal portion extending to a distal end, said introducer distal portion received in said dilator passageway and extending substantially along a length of said dilator to said tapered distal portion, said introducer structured and arranged relative to said dilator such that upon a proximal movement of said dilator relative to said introducer, said tapered distal tip of said dilator splits whereby said introducer distal portion extends through said split dilator portion, said introducer proximal end extending beyond said dilator proximal portion in a proximal direction, said introducer being dimensioned for receiving said implantable member therein; and a handle mechanism arranged to receive said proximal portion of said dilator, said handle mechanism including a respective gripping mechanism engaged with each of said at least one tab for initiating said proximal movement of said dilator relative to said introducer upon a rotation of said gripping mechanism, and an activator engaged with said gripping mechanism for initiating said rotation of said gripping mechanism, wherein said handle includes a clamp member for releasably receiving said proximal portion of said introducer, wherein said at least one tab comprises a pair of tabs and said handle mechanism comprises a pair of gripping mechanisms, each of said gripping mechanisms engaged with a respective one of said tabs, wherein said at least one tab comprises a pair of tabs and said handle mechanism comprises a pair of gripping mechanisms, each of said gripping mechanisms engaged with a respective one of said tabs, wherein said handle mechanism further comprises an elongated nose portion arranged therealong, said nose portion including a distally tapered portion structured and arranged to receive said dilator proximal portion upon said proximal movement, and configured such that said dilator proximal portion splits upon movement thereover, wherein said activator comprises a trigger member movably engaged with said nose portion, wherein said handle further comprises a biasing member for moving said dilator in a distal direction upon a release of said activator.

2. The delivery system of claim 1, wherein said handle mechanism includes a structure for splitting said proximal portion of said dilator upon said proximal movement of said dilator, said proximal portion splitting from a proximal end of said dilator in a distal direction, and said distal portion splitting independent of the splitting of the proximal portion.

3. The delivery system of claim 1, wherein each of said gripping mechanisms comprises a jaw portion engaged with said tab for initiating said proximal movement of said dilator, and a stop portion for controlling an amount of rotation of said gripping mechanism.

4. The delivery system of claim 1, wherein said handle comprises a respective frame member for receiving each of said gripping mechanisms, each of said gripping mechanisms further comprising a stop portion engageable with said frame member for controlling an amount of rotation of said gripping mechanism.

5. The delivery system of claim 1, wherein said dilator includes a slit along said distal portion for facilitating a splitting of said dilator distal portion.

6. A delivery system for delivering an implantable member to a target site in the body of a patient, comprising:
   a splittable elongated dilator having a proximal portion, a distal portion, and a passageway extending therebetween, said passageway dimensioned for receiving said implantable member therein, said proximal portion including a pair of tabs extending therefrom, said distal portion extending to a tapered distal tip, said distal portion being structured for splitting to facilitate delivery of said implantable member to said target site; and
   a handle engaged with said dilator proximal portion, said handle including a respective gripping mechanism engaged with each of said tabs for initiating a proximal movement of said dilator upon activation of said gripping mechanisms, and an activator for said gripping mechanisms, said handle including a structure for splitting said proximal portion of said dilator toward said dilator distal end upon said proximal movement of said dilator,
   wherein said splitting structure of said handle comprises an elongated nose member having a distally tapered portion for receiving said dilator proximal portion, and
   wherein said activator comprises a trigger member movably engaged with said nose member, wherein each of said gripping mechanisms comprises a jaw portion arranged to receive a respective one of said tabs, said handle structured such that a length of said dilator is movably received therealong upon activation of said trigger member.

7. The delivery system of claim 6, further comprising an introducer having a proximal portion and a distal portion, said introducer distal portion received in said dilator passageway and extending substantially along a length of said dilator to said tapered distal tip, said introducer structured and arranged relative to said dilator such that upon said proximal movement of said dilator, said tapered distal tip of said dilator splits whereby said introducer distal portion extends through said split dilator portion, said introducer proximal portion extending beyond said dilator proximal portion in a proximal direction, said introducer being dimensioned for receiving said implantable member therein.

8. The delivery system of claim 6, wherein said handle further comprises a biasing member for moving said dilator in a distal direction upon a release of said trigger member.

9. A delivery system for deploying an implantable medical member to a target site within the body of a patient, comprising:
   an elongated dilator having a proximal portion, a distal portion, and a passageway extending therebetween, said proximal portion including at least one tab extending from a proximal end thereof, said distal portion tapering to a distal tip, said distal portion being splittable to facilitate delivery of said implantable medical member to said target site;
   an introducer having a proximal portion and a distal portion, said proximal portion extending to a proximal end and said distal portion extending to a distal end, said introducer distal portion received in said dilator passageway and extending substantially along a length of said dilator to said tapered distal portion, said introducer structured and arranged relative to said dilator such that upon a proximal movement of said dilator relative to said introducer, said tapered distal tip of said dilator splits whereby said introducer distal portion extends through said split dilator portion, said introducer proximal end extending beyond said dilator proximal portion in a proximal direction, said introducer being dimensioned for receiving said implantable member therein; and
   a handle mechanism arranged to receive said proximal portion of said dilator, said handle mechanism including a respective gripping mechanism engaged with each of said at least one tab for initiating said proximal movement of said dilator relative to said introducer upon a rotation of said gripping mechanism, and an activator engaged with said gripping mechanism for initiating said rotation of said gripping mechanism,
   wherein said at least one tab comprises a pair of tabs and said handle mechanism comprises a pair of gripping mechanisms, each of said gripping mechanisms engaged with a respective one of said tabs,
   wherein said handle mechanism further comprises an elongated nose portion arranged therealong, said nose portion including a distally tapered portion structured and arranged to receive said dilator proximal portion upon said proximal movement, and configured such that said dilator proximal portion splits upon movement thereover, wherein said activator comprises a trigger member movably engaged with said nose portion, and wherein said handle further comprises a biasing member for moving said dilator in a distal direction upon a release of said activator.

10. The delivery system of claim 9, wherein each of said gripping mechanisms comprises a jaw portion engaged with said tab for initiating said proximal movement of said dilator, and a stop portion for controlling an amount of rotation of said gripping mechanism.

11. The delivery system of claim 9, wherein said handle comprises a respective frame member for receiving each of said gripping mechanisms, each of said gripping mechanisms further comprising a stop portion engageable with said frame member for controlling an amount of rotation of said gripping mechanism.

12. The delivery system of claim 9, wherein said dilator includes a slit along said distal portion for facilitating a splitting of said dilator distal portion.

13. The delivery system of claim 9, wherein said handle includes a clamp member for releasably receiving said proximal portion of said introducer.

* * * * *

UNITED STATES PATENT AND TRADEMARK OFFICE
CERTIFICATE OF CORRECTION

PATENT NO.        : 9,131,959 B2
APPLICATION NO.   : 13/214578
DATED             : September 15, 2015
INVENTOR(S)       : Goode et al.

It is certified that error appears in the above-identified patent and that said Letters Patent is hereby corrected as shown below:

In the Claims

In column 9, Claim 1, lines 20 through 23, delete the following language:

"wherein said at least one tab comprises a pair of tabs and said handle mechanism comprises a pair of gripping mechanisms, each of said gripping mechanisms engaged with a respective one of said tabs,"

Signed and Sealed this
Nineteenth Day of April, 2016

Michelle K. Lee
*Director of the United States Patent and Trademark Office*